(12) United States Patent
Chang

(10) Patent No.: US 8,394,057 B2
(45) Date of Patent: Mar. 12, 2013

(54) SAFETY SYRINGE

(75) Inventor: Yu-Sheng Chang, Kaohsiung (TW)

(73) Assignee: Concept Spirit Alliance Ltd., Belize (BZ)

( * ) Notice: Subject to any disclaimer, the term of this patent is extended or adjusted under 35 U.S.C. 154(b) by 1157 days.

(21) Appl. No.: 12/254,412

(22) Filed: Oct. 20, 2008

(65) Prior Publication Data

US 2010/0100053 A1    Apr. 22, 2010

(51) Int. Cl.
*A61M 5/00* (2006.01)
*A61M 5/32* (2006.01)

(52) U.S. Cl. ...................................................... 604/110

(58) Field of Classification Search .................. 604/110, 604/192–197

See application file for complete search history.

(56) References Cited

U.S. PATENT DOCUMENTS

| 5,575,774 | A | 11/1996 | Chen | |
|---|---|---|---|---|
| 2006/0106339 | A1* | 5/2006 | Mastorakis | 604/110 |
| 2006/0106340 | A1* | 5/2006 | Goossens et al. | 604/110 |

* cited by examiner

*Primary Examiner* — Kevin C Sirmons
*Assistant Examiner* — Andrew Gilbert
(74) *Attorney, Agent, or Firm* — Burr & Brown

(57) ABSTRACT

A safety syringe has a barrel, an inner needle hub, an outer needle hub, a plunger. The barrel has a distal end and a spout. The spout is formed axially on and protrudes the distal end. The plunger is mounted in the barrel and has a mounting protrusion being formed axially on the distal end of the plunger. The outer needle hub is mounted on the spout of the barrel and has a mounting chamber formed in the outer needle hub. The inner needle hub is mounted in the mounting chamber of the outer needle hub and has multiple resilient wing sections that are mounted in the mounting protrusion. Therefore, the inner needle hub may be withdrawn without touching the needle or outer needle hub and disposed of safely.

18 Claims, 18 Drawing Sheets

SAFETY SYRINGE

BACKGROUND OF THE INVENTION

1. Field of the Invention

The present invention relates to a safety syringe, especially to a safety syringe that can retract the used needle easily.

2. Description of the Prior Arts

U.S. Pat. No. 5,575,774 disclosed a safety syringe with retractable needle to reduce injuries to health care workers.

The safety syringe in accordance with the prior art has a barrel, a needle holder and a plunger. The barrel has an inner surface and an inside flange. The inside flange is formed on the inner surface and has a diameter. The needle holder has a holding space and a retaining hole. The holding space corresponds to the inside flange and has a diameter. The diameter of the holding space is larger than the diameter of the inside flange. The plunger has a retainer rod formed on a proximal end of the plunger. The retainer rod corresponds to the retaining hole. During use, the retainer rod is pressed into the retaining hole of the needle holder so the retainer rod engages the needle holder. After use, the plunger may be extended, pulling the needle into the barrel for improved safety.

However, the holding space of the needle holder and the inside flange of the barrel must be manufactured accurately to ensure correct fitting and combined with correct tightness to ensure correct functioning. Otherwise, the needle can fall off the needle holder or can not be pulled into the barrel so that the health care workers injured.

To overcome the shortcomings, the present invention provides a safety syringe to mitigate or obviate the aforementioned problems.

SUMMARY OF THE INVENTION

The main objective of the present invention is to provide a safety syringe that can retract the used needle easily so that the user is able to readily.

A safety syringe in accordance with the present invention has a barrel, an inner needle hub, an outer needle hub, a plunger. The barrel has a distal end and a spout. The spout is formed axially on and protrudes the distal end. The plunger is mounted in the barrel and has a mounting protrusion being formed axially on the distal end of the plunger. The outer needle hub is mounted on the spout of the barrel and has a mounting chamber formed in the outer needle hub. The inner needle hub is mounted in the mounting chamber of the outer needle hub and has multiple resilient wing sections that are mounted in the mounting protrusion. Therefore, the inner needle hub may be withdrawn without touching the needle or outer needle hub and disposed of safely.

Other objectives, advantages and novel features of the invention will become more apparent from the following detailed description when taken in conjunction with the accompanying drawings.

BRIEF DESCRIPTION OF THE DRAWINGS

FIG. 14 is an operational cross sectional view of the safety syringe in FIG. 13A, showing a needle retracted by a plunger in;

FIG. 17 is an operational cross sectional view of the second embodiment of the safety syringe in FIG. 15A, showing a needle retracted by a plunger in.

DETAILED DESCRIPTION OF THE PREFERRED EMBODIMENTS

Figure 1:
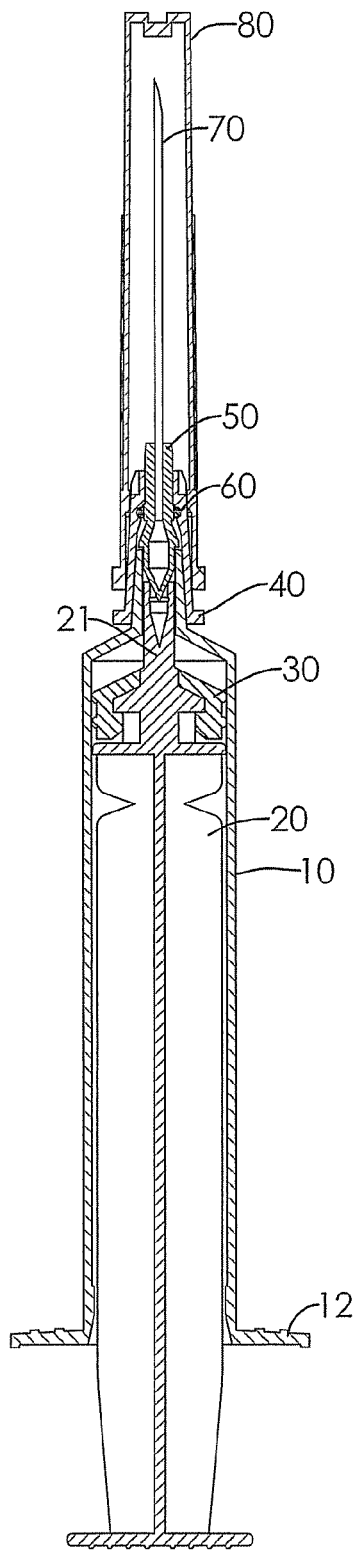
FIG. 1 is a cross sectional view of a first embodiment of a safety syringe in accordance with the present invention.
Figure 2:
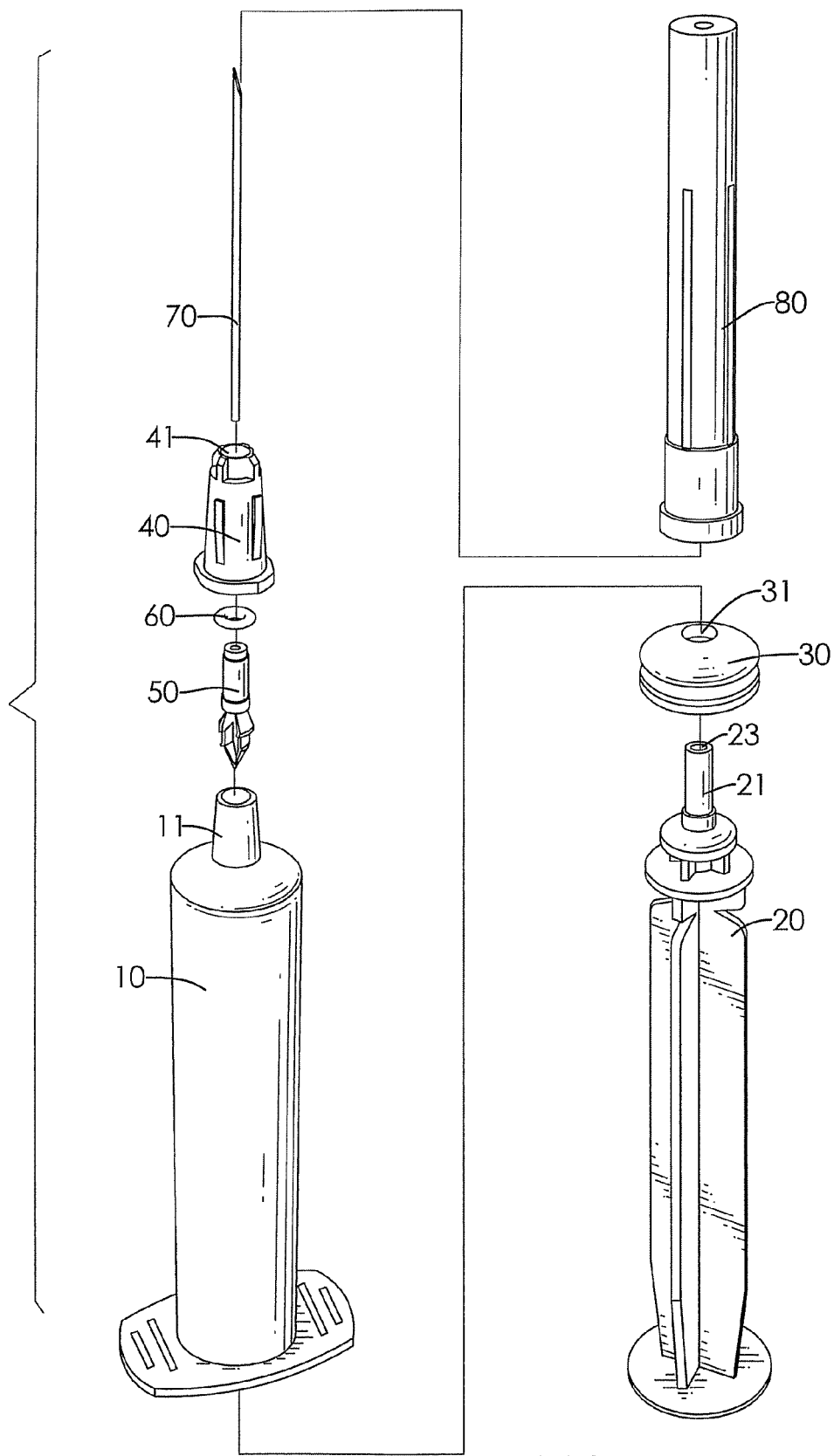
FIG. 2 is an exploded perspective view of the safety syringe in FIG. 1.

With reference to FIGS. 1 and 2, a safety syringe in accordance with the present invention has a barrel (10), a plunger (20), a plug (30), an outer needle hub (40), an inner needle hub (50), a sealing ring (60), a needle (70) and a cover (80).

Figures 3, 4:
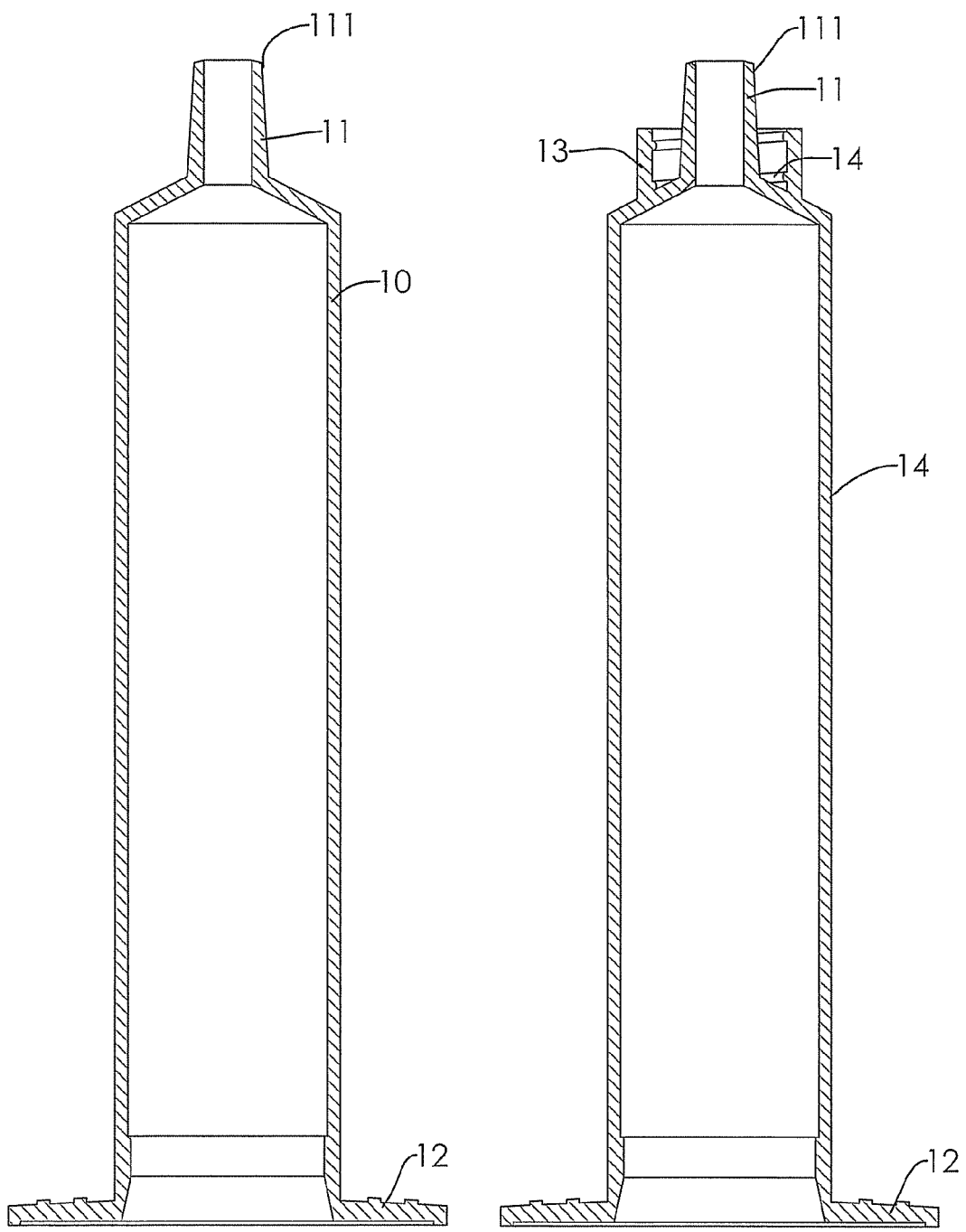
FIG. 3 is a cross sectional view of a safety syringe in FIG. 1.
FIG. 4 is a cross sectional view of a barrel of a second embodiment of a safety syringe in accordance with the present invention.

With further reference to FIG. 3, the barrel (10) is hollow and has a proximal end, a distal end, a spout (11) and two finger rests (12). With further reference to FIG. 4, the barrel (10) may further have an outer hub mount (13). The spout (11) is formed axially on and protrudes from the distal end and has an outer diameter and an inner diameter. On the top end of the spout (11) further formed a tapered surface (111). The finger rests (12) are formed on and protrude oppositely from the proximal end. The outer hub mount (13) is annular, is formed on the distal end around the spout (11) of the barrel (10) and has an inner thread (14).

Figures 5A, 5B:
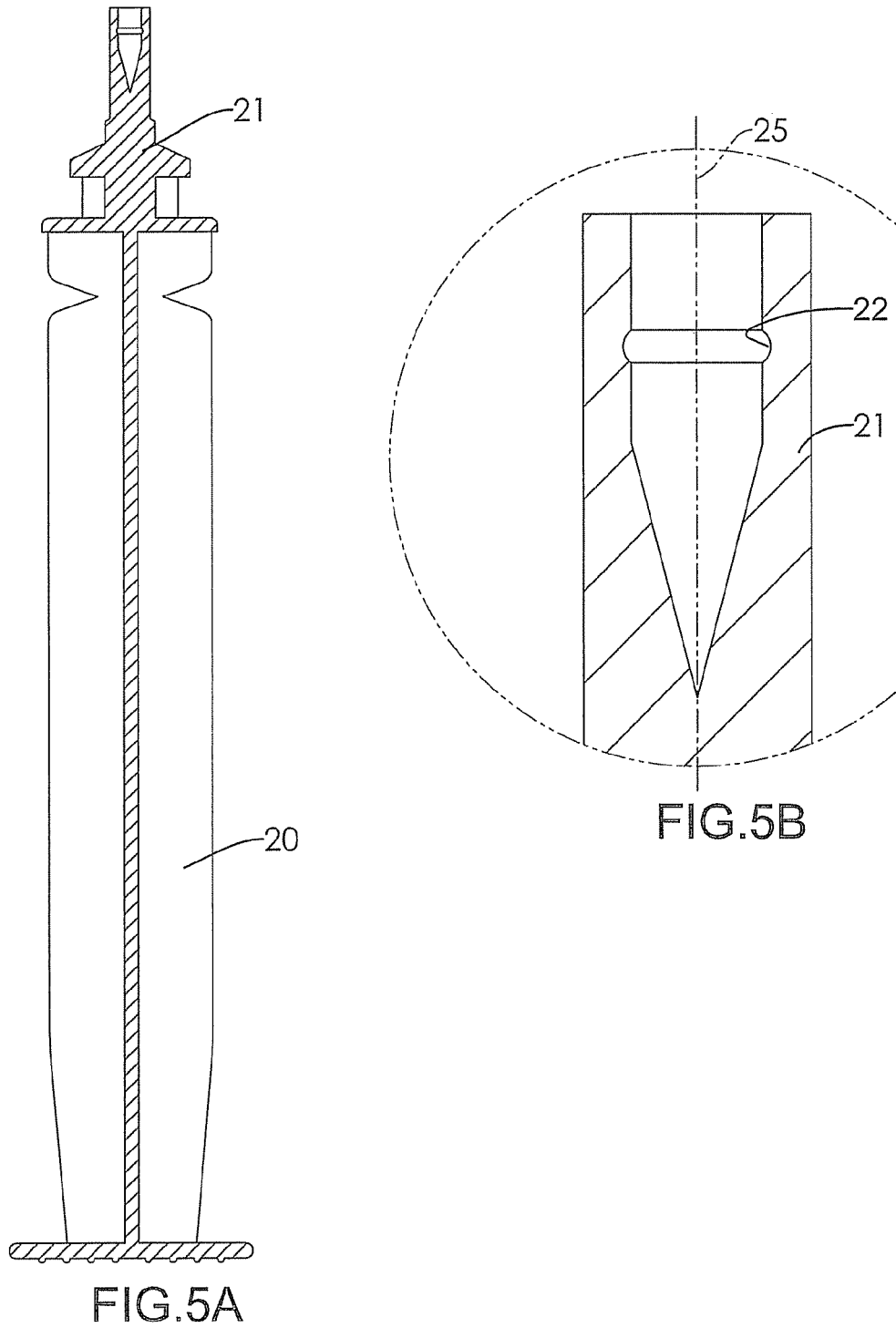
FIG. 5A is a cross sectional view of a plunger of the safety syringe in FIG. 1.
FIG. 5B is an enlarged cross sectional of the plunger of the safety syringe in FIG. 5A.

With further reference to FIGS. 5A and 5B, the plunger (20) is mounted in the barrel (10) and has a distal end and a mounting protrusion (21) and may further comprise a pre-cut.

The mounting protrusion (21) is centrally formed axially on the distal end of the plunger (20) and has an engaging hole (23), a groove (22), a cross section and an axis (25). The engaging hole (23) is defined axially in the mounting protrusion (21) and has an inner surface and a V-shaped cross section that is parallel with and axially-symmetrical to the axis (25) of the mounting protrusion (21). The groove (22) is formed circumferentially around the inner surface of the plunger (20). The pre-cut is formed in the plunger (20) adjacent to the distal end and allows the plunger (20) to be snapped off near the distal end after use.

Figure 6:
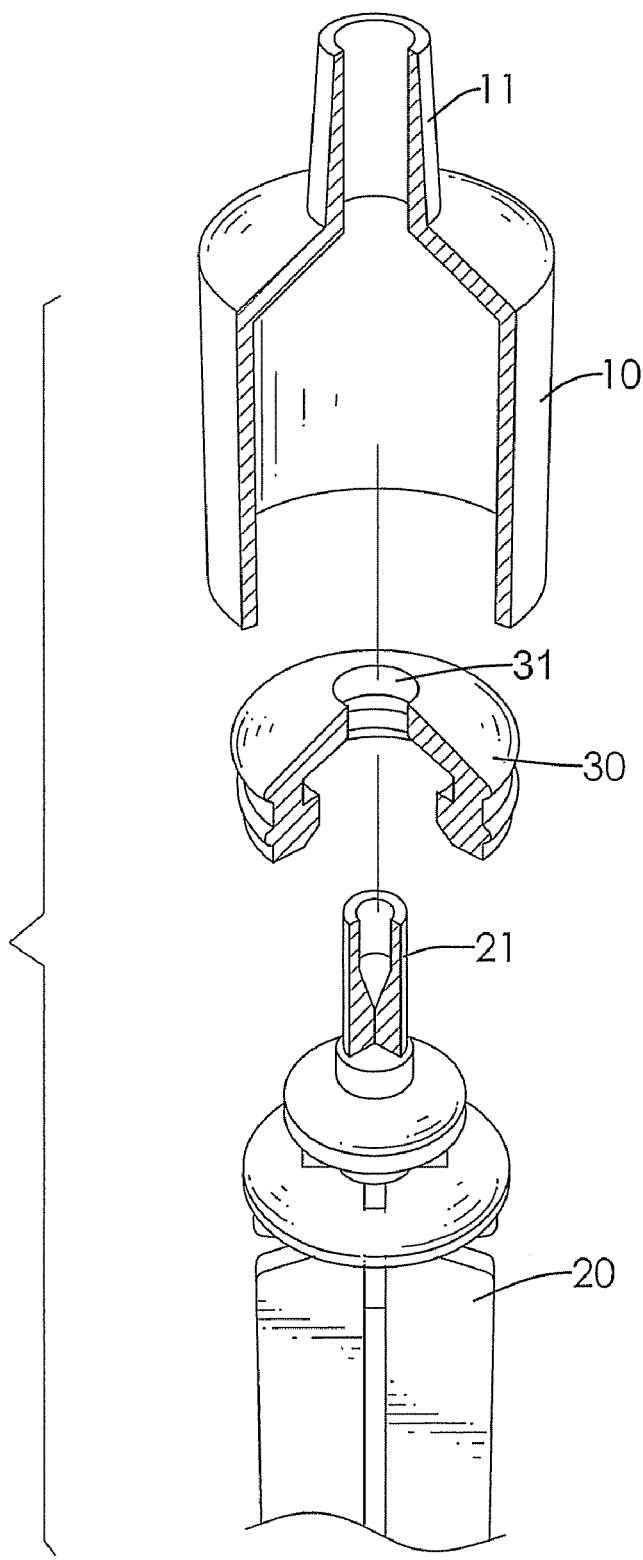
FIG. 6 is an enlarged, exploded perspective view in partial section of the plunger and barrel of the safety syringe in FIG. 1.

With further reference to FIG. 6, the plug (30) is a disk, may be resilient material such as rubber or plastic, is mounted around the mounting protrusion (21) of the plunger (20) and has a through hole (31). The through hole (31) is centrally formed axially through the plug (30) and is mounted around the mounting protrusion (21) of the plunger (20).

Figure 7:
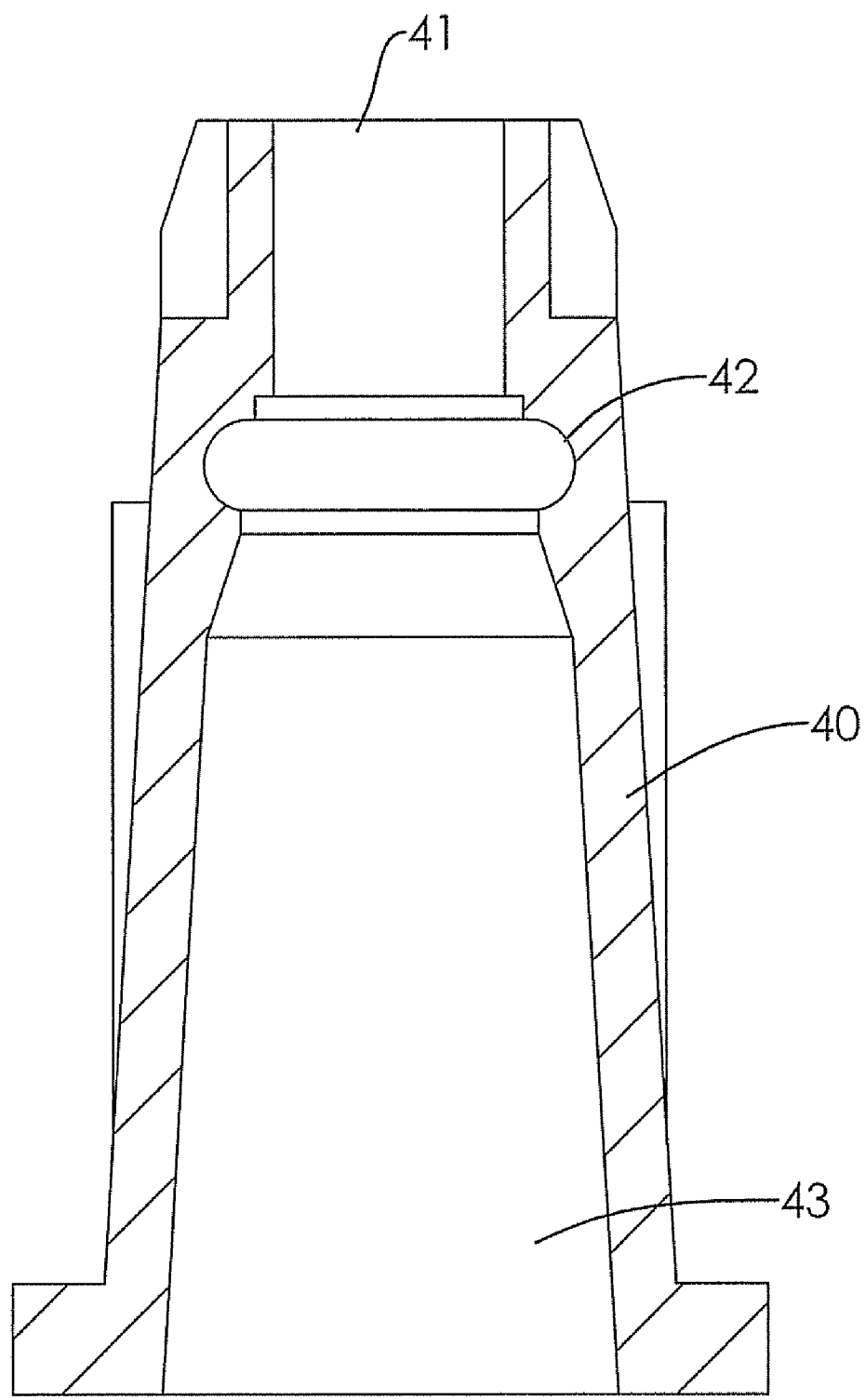
FIG. 7 is a cross sectional view of an outer needle hub of the safety syringe in FIG. 1.

With further reference to FIG. 7, the outer needle hub (40) is mounted on the spout (11) of the barrel (10) and has an inner surface, a connecting end, a mounting end, a hub hole (41), a ring groove (42) and a mounting chamber (43). The hub hole (41) is formed through the connecting end of the outer needle hub (40). The ring groove (42) is formed in the inner surface of the outer needle hub (40) between the hub hole (41) and the mounting chamber (43). The mounting chamber (43) is formed in the mounting end of the outer needle hub (40), communicates with the hub hole (41) and may be tapered toward the ring groove (42).

Figure 8:
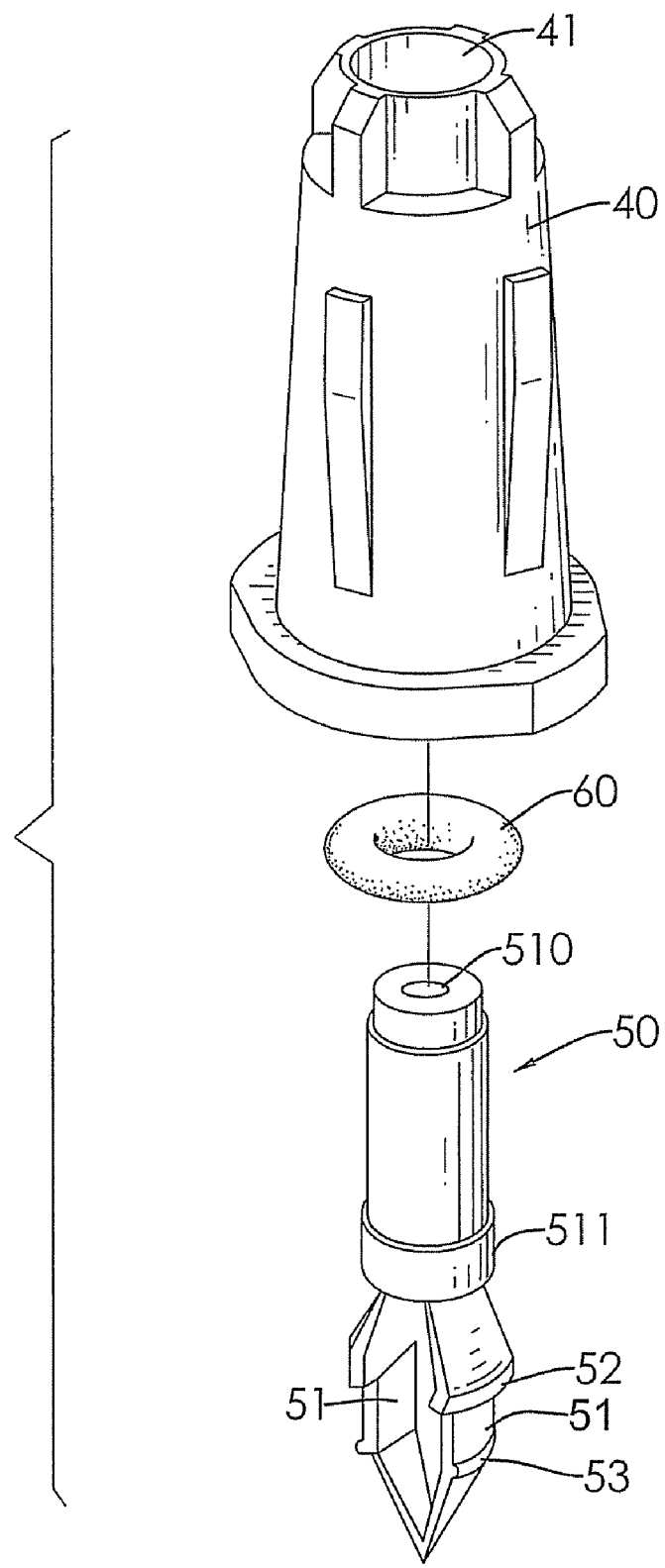
FIG. 8 is an exploded perspective view of the outer needle hub, an inner needle hub and a sealing ring of the safety syringe in FIG. 1.
Figure 9:
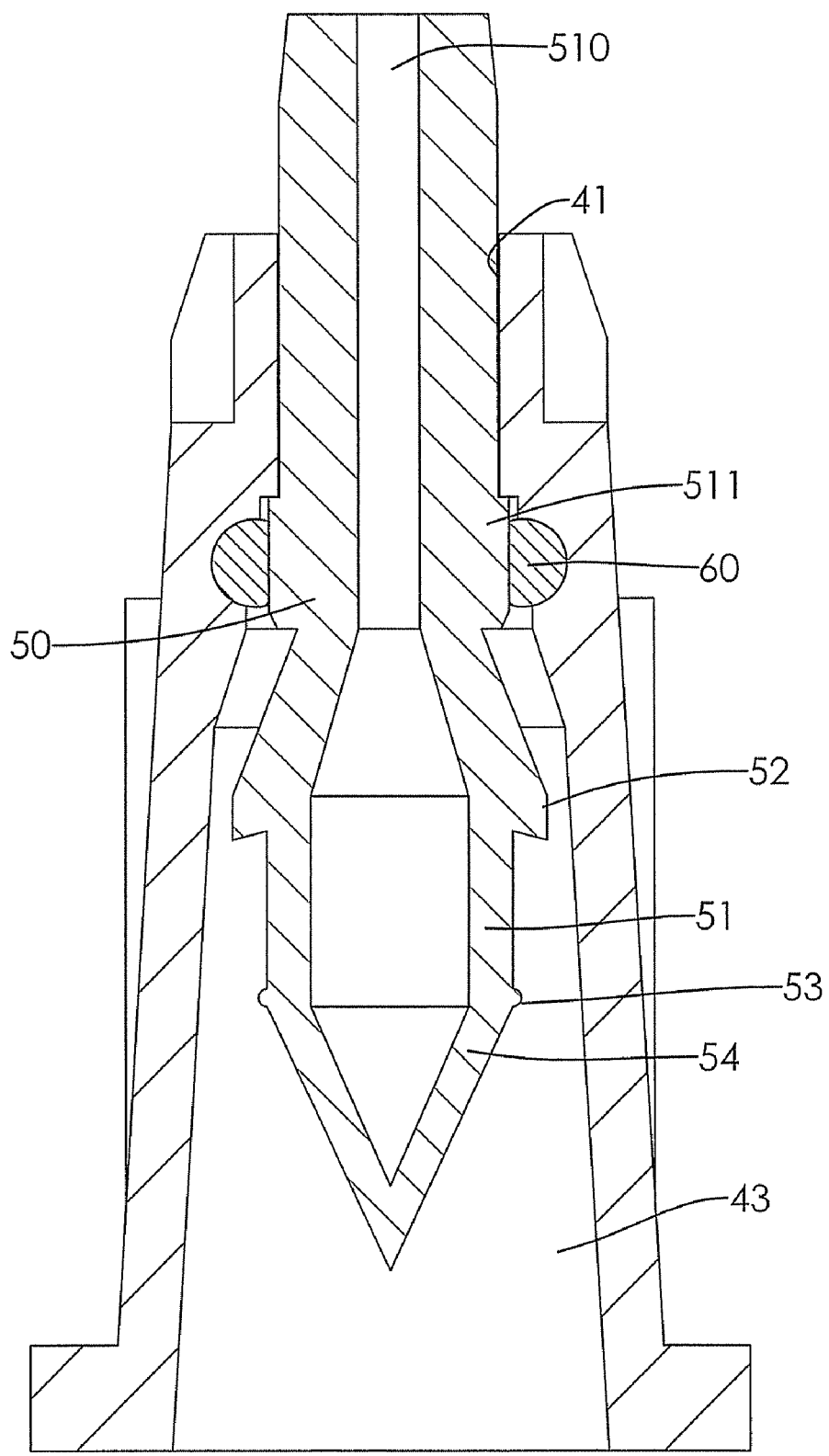
FIG. 9 is a cross sectional view showing the outer needle hub, the inner needle hub and the sealing ring of the safety syringe in FIG. 1.

With further reference to FIGS. 8 and 9, the inner needle hub (50) may be cylindrical, is mounted through and extends out of the hub hole (41) of the outer needle hub (40), is mounted in the mounting chamber (43) and has an outside end, an inside end, a needle hole (510), an outer surface, a shoulder (511) and at least two wing sections (51).

The needle hole (510) is defined through the inner needle hub (50). The shoulder (511) of the inner needle hub (50) is formed on and protrudes radially from the inner needle hub (50) adjacent to the inside end, is larger than and abuts the hub hole (41) of the outer needle hub (40) and is aligned with the ring groove (42).

The wing sections (51) are formed on and protrude from the shoulder (511) of the inner needle hub (50), extend in the mounting chamber (43) of the outer needle hub (40) and may be jointed pivotally. Each wing section (51) is resilient and has a collar (52) and an arm (54). The collar (52) is formed on and protrudes at an angle away from the shoulder (511) of the inner needle hub (50). The collar (52) further has a inner slope (521) being formed on an end opposed to the shoulder (511). The inner slope (521) protrudes out from the wing section (51). The inner slope (521) abuts to the tapered surface (111). The width of the tapered surface (111) is wider than the width of the inner slope (521).

Figure 10:
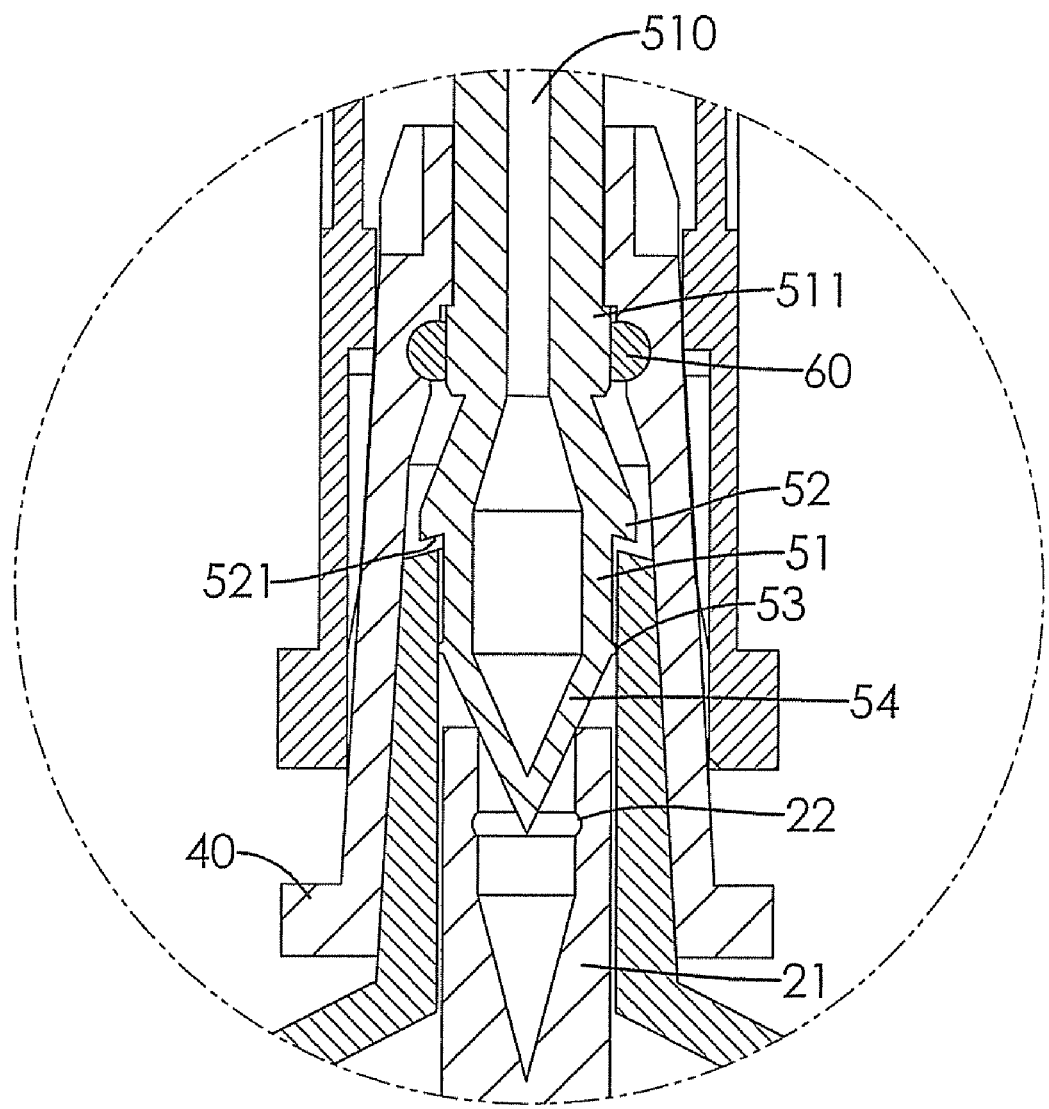
FIG. 10 is an enlarged cross sectional view of the inner needle hub of the safety syringe in FIG. 1.
Figures 11A, 11B:
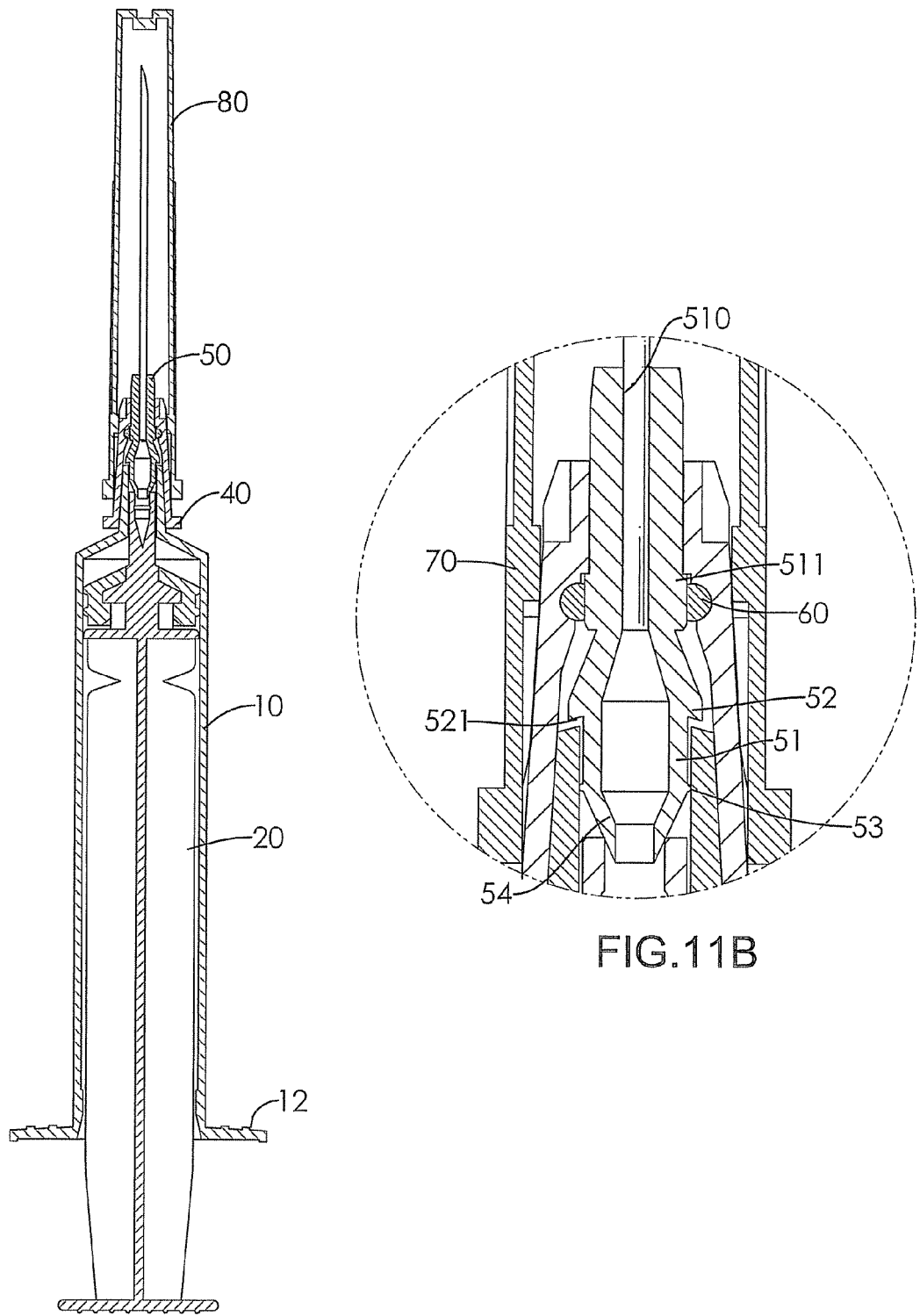
FIG. 11A is a cross sectional side view of a third embodiment of a safety syringe in accordance with the present invention.
FIG. 11B is an enlarged cross sectional view of the inner needle hub in FIG. 11A.

The arm (54) is formed on, protrudes from and is narrower than the collar (52) so forms a rim there between and has an outer surface, a tip and a boss (53), wherein the rim has a tapered inner surface defining an inner space. The tip is formed on the arm (54) and beveled inwards to guide the wing section (51) into the mounting protrusion (21) of the plunger (20). With further reference to FIGS. 9 to 11B, the tips of the opposing arms (54) may be joined pivotally, as shown in FIGS. 1 and 10. Alternatively, the tips of the arms (54) may be separate, as shown in FIGS. 11A and 11B. The boss (53) is formed on the outer surface of the arm (54) and selectively engages the groove (22) of the mounting protrusion (21) of the plunger (20).

The tapered surface (111) of the spout (11) abuts the inner slope (521) of the collar (52) and holds the inner slope (521) in position when assembling the out needle hub (40) and inner needle hub (50) to the spout (11) of the barrel (10) before utilization of the syringe.

The sealing ring (60) is mounted in the ring groove (42) of the outer needle hub (40) and between the inner needle hub (50) and the outer needle hub (40) to ensure a seal is maintained.

The needle (70) is hollow and is mounted in the needle hole (510) of the inner needle hub (50).

The cover (80) is an open cylindrical container mounted on the outer needle hub (40) and holding the needle (70).

Figure 12:
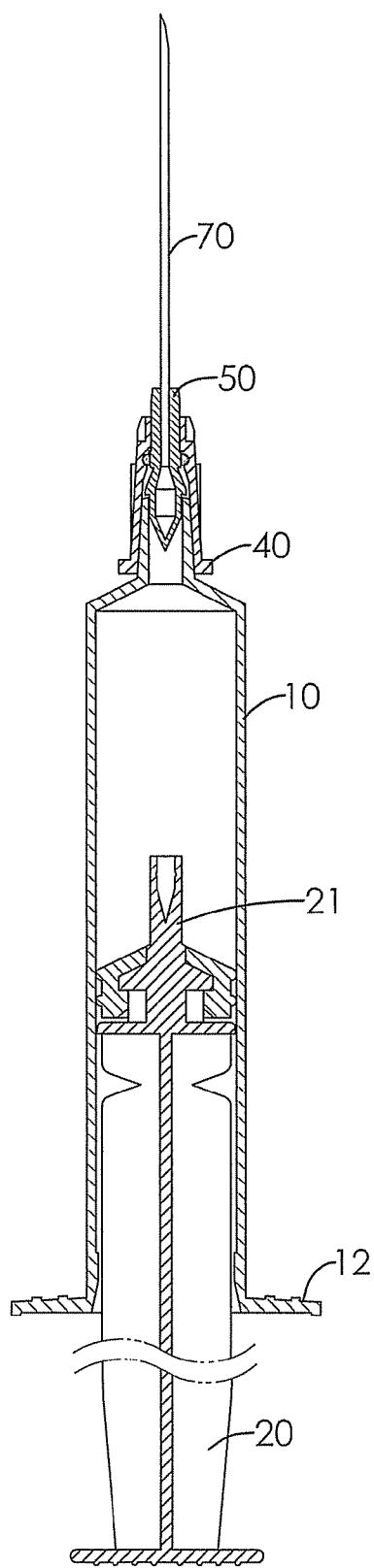
FIG. 12 is an operational cross side view of the safety syringe in FIG. 1 shown drawing liquid.
Figures 13A, 13B:
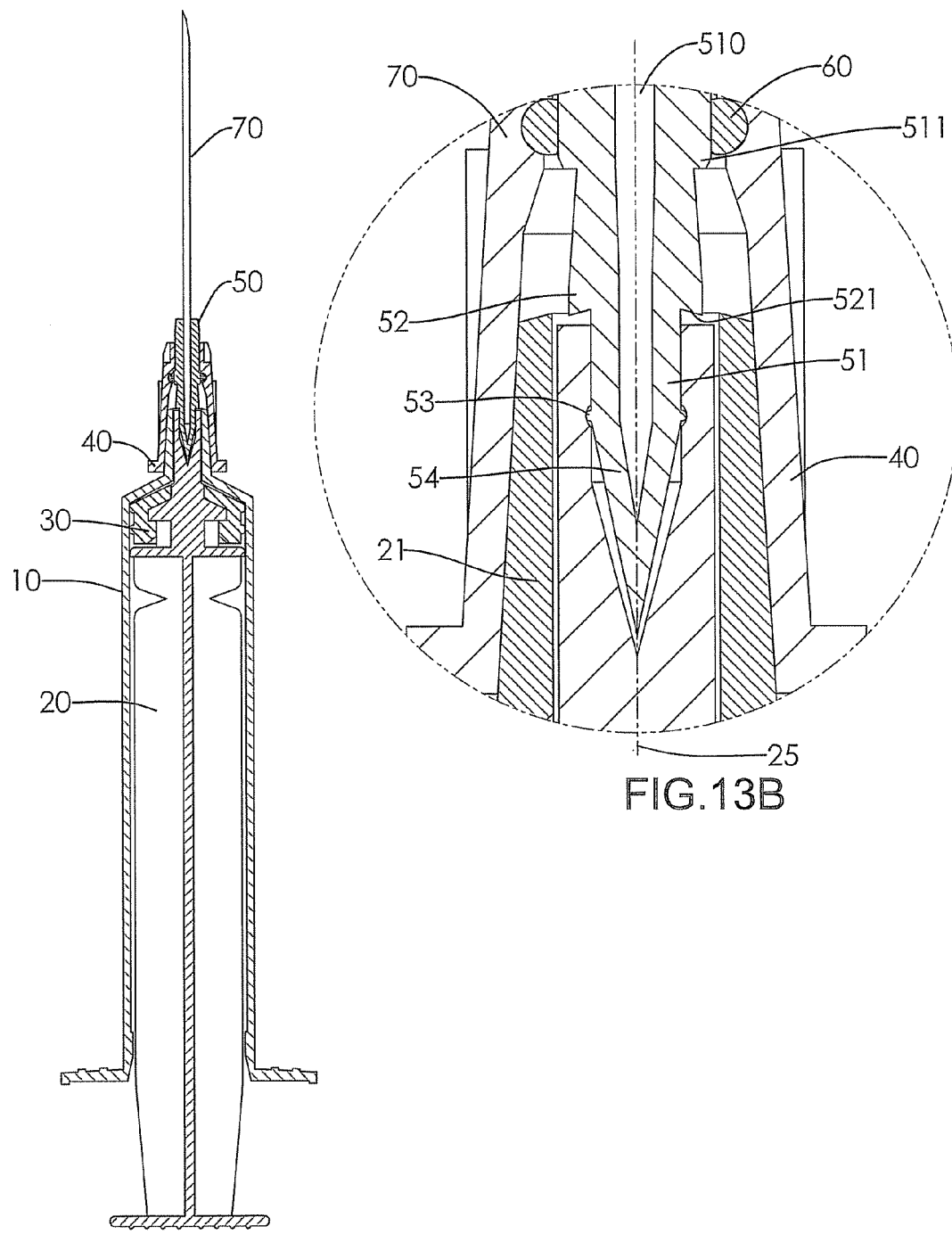
FIG. 13A is an operational cross sectional view of the safety syringe in FIG. 1, showing the inner needle hub engaging a mounting protrusion after injection in FIG. 1.
FIG. 13B is an enlarged cross sectional view of the inner needle hub of the safety syringe in FIG. 13A.
Figure 14:
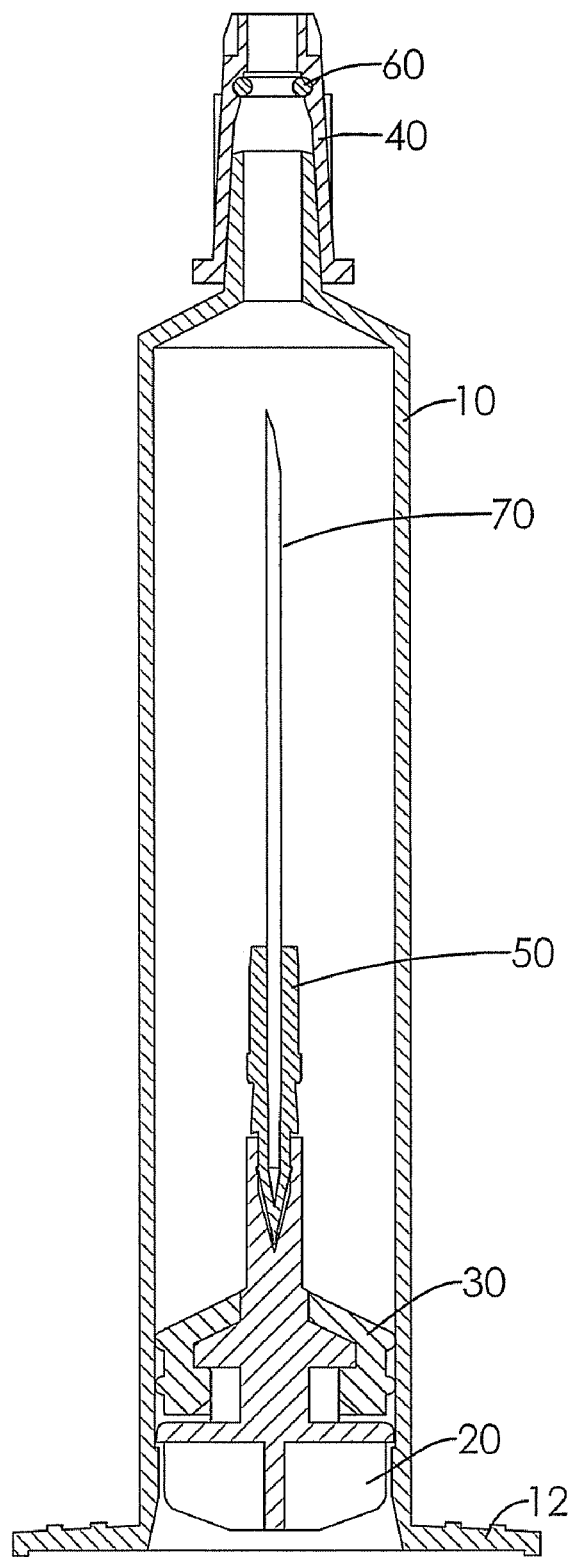

The With further reference to FIGS. 12 to 14, the outer needle hub (40) containing the needle (70) mounted in the inner needle hub (50) and being mounted in the cover (80), is pressed on the spout (11) of the barrel (10) and until the collars (52) of the wing sections (51) abut the spout (11). With reference to FIGS. 3 and 4, the outer needle hub (40) may be screwed into the inner thread (14) of the outer hub mount (13) or mounted on the spout (11) of the barrel (10) before the syringe is utilized. Therefore, the plunger (20) can be withdrawn to pull up medicine. Then, the plunger (20) is pressed to the distal end of the barrel (10) until the wing section (51) is compressed and guided into the mounting protrusion (21) of the plunger (20). The bosses (53) of the wing sections (51) are mounted in the groove (22) of the mounting protrusion (21) of the plunger (20) and the inner slope (521) is separated from the tapered surface (111) allowing the collar (52) to be received into the spout (11) so that withdrawing the plunger (20) pulls the needle (70) and inner needle hub (50) into the barrel (10) to avoid injuries to health care workers. Finally, the plunger (20) may be snapped off at the pre-cut.

Figure 15A:
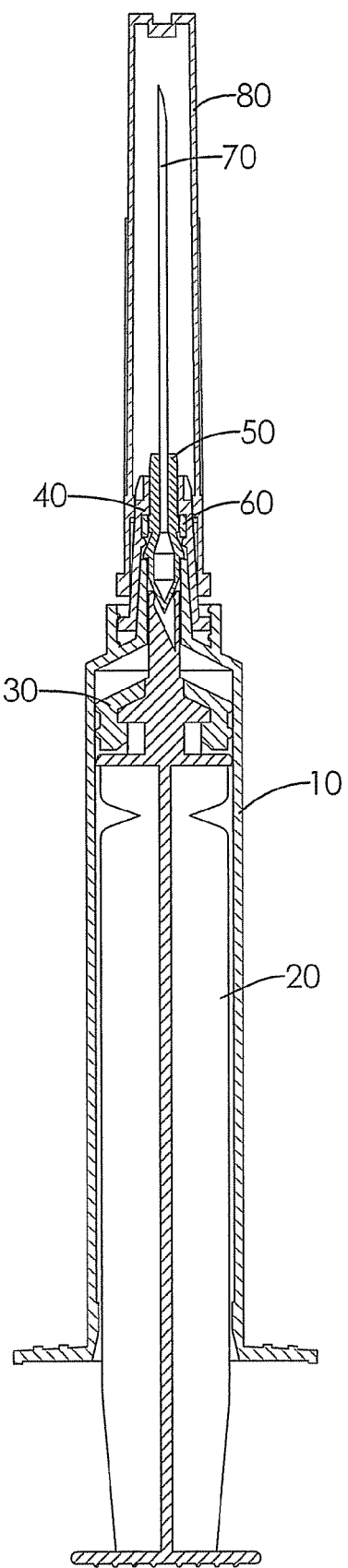
FIG. 15A is an operational cross sectional view of the safety syringe, showing the inner needle hub engaging a oblique mounting protrusion.
Figure 15B:
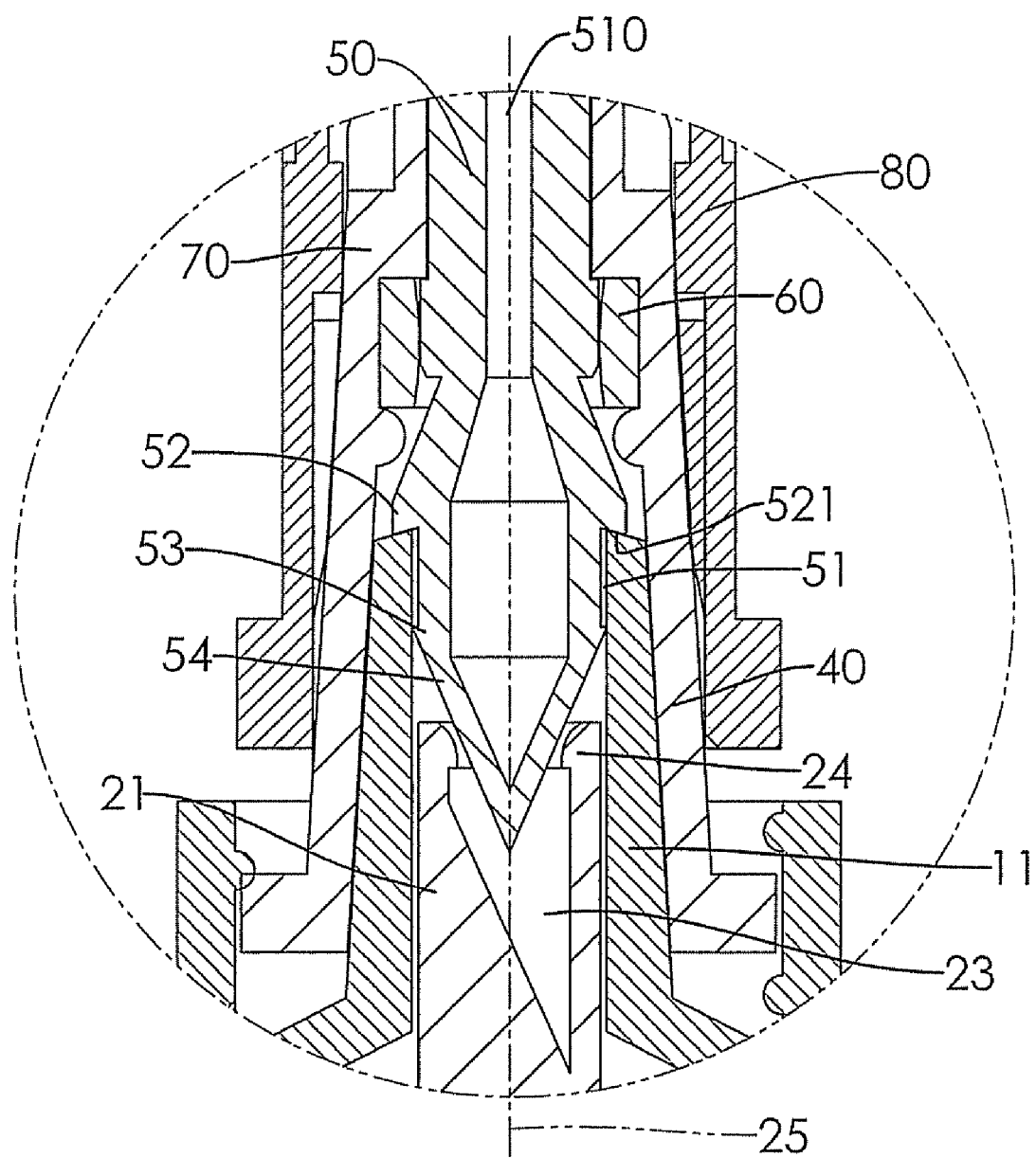
FIG. 15B is an enlarged cross sectional view of the inner needle hub of the safety syringe in FIG. 15A.
Figure 16A:
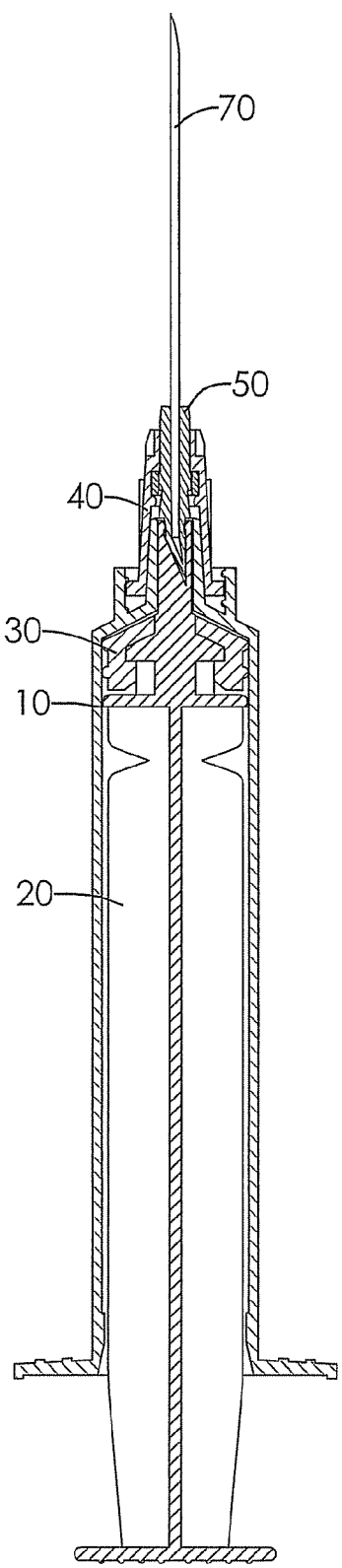
FIG. 16A is an operational cross sectional view of the safety syringe, showing the inner needle hub engaging a oblique mounting protrusion after injection in FIG. 15A.
Figure 16B:
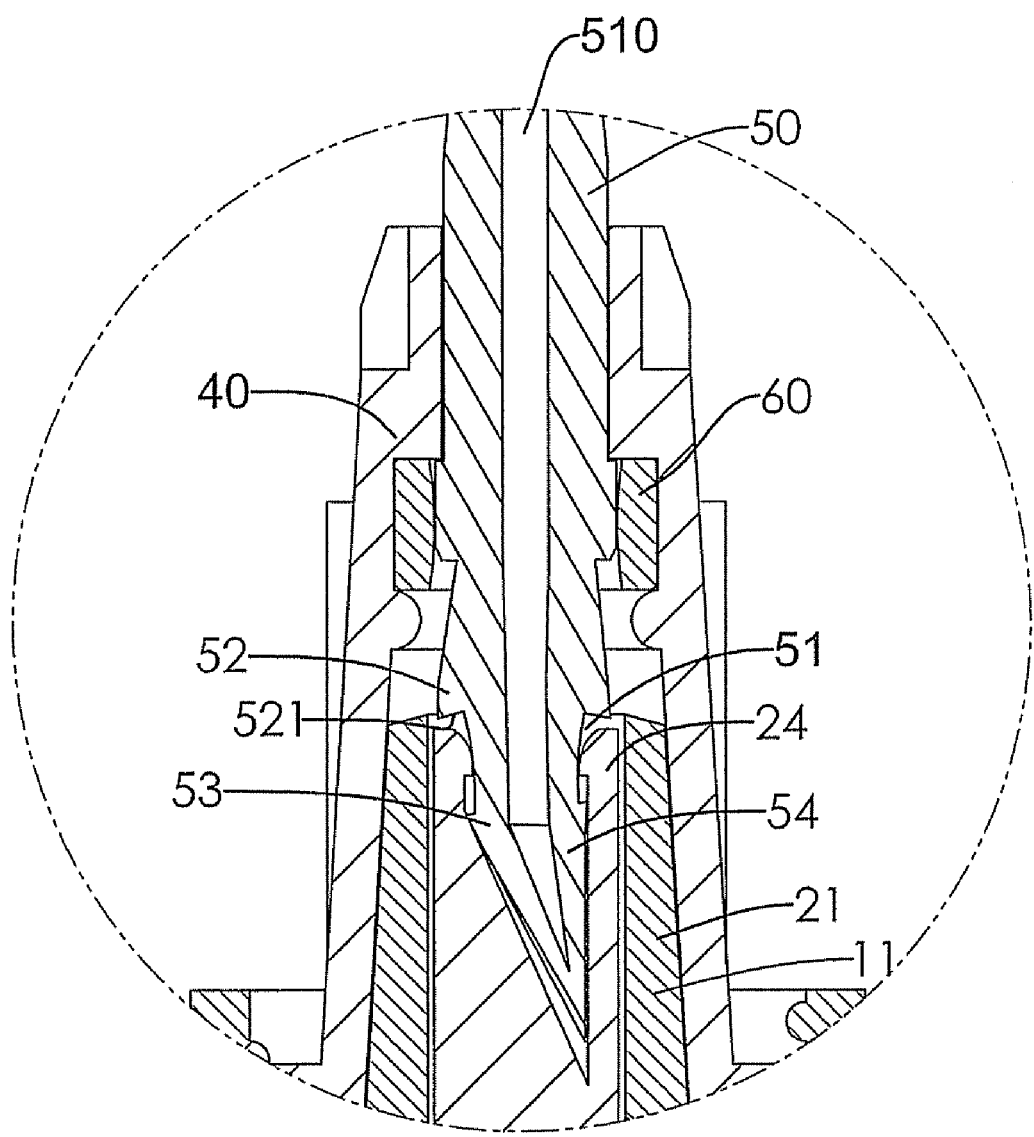
FIG. 16B is an enlarged cross sectional view of the inner needle hub of the safety syringe in FIG. 16A.

With further reference to FIGS. 15A to 15B, a second embodiment of the safety syringe is similar to the first embodiment and the mounting protrusion (21) of the second embodiment has an engaging hole (23), a hook (24) and an axis (25). The engaging hole (23) is defined axially in the mounting protrusion (21) and has a distal end, an inner surface and a V-shaped cross section that is inclined to the axis (25) of the engaging hole (23). The hook (24) may be annular and is formed on the inner surface at the distal end of the engaging hole (23) of the plunger (20).

Figure 17:
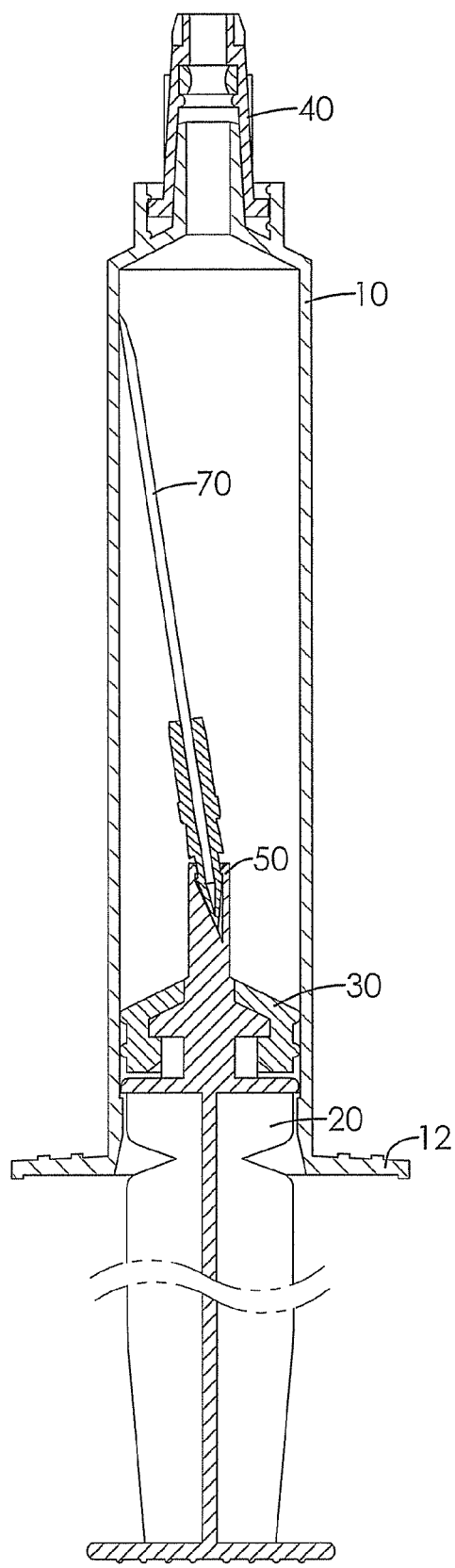

With further reference to 16A and 16B, the outer needle hub (40) containing the needle (70) mounted in the inner needle hub (50) and being mounted in the cover (80), is pressed on the spout (11) of the barrel (10) and until the collars (52) of the wing sections (51) abut the spout (11). With reference to FIGS. 3 and 4, the outer needle hub (40) may be screwed into the inner thread (14) of the outer hub mount (13) or mounted on the spout (11) of the barrel (10) before the syringe is utilized. Therefore, the plunger (20) can be withdrawn to pull up medicine. Then, the plunger (20) is pressed to the distal end of the barrel (10) until the wing section (51) is compressed and guided into the mounting protrusion (21) of the plunger (20). The bosses (53) and arm (54) of the wing sections (51) are inclined and mounted in the engaging hole (23) of the mounting protrusion (21) of the plunger (20) and the inner slope (521) is separated from the tapered surface (111) allowing the collar (52) to be received into the spout (11) so that withdrawing the plunger (20) pulls the needle (70) and inner needle hub (50) into the barrel (10), because the engaging hole (23) is in engagement with in the bosses (53) and arm (54), the needle (70) and inner needle hub (50) are inclined relative to the barrel (10). When the needle (70) and inner needle hub (50) is inclined to and fully received in the barrel (10), as show in FIG. 17, a forward movement of the plunger (20) together with the inner needle hub (50) results in the needle (70) being bent inside the barrel (10) such that the safety syringe of the present invention is able to be disposed of safely.

The safety syringe in accordance with the present invention has the following advantages:

1. The safety syringe can provide a simple and convenient way to pull the needle (70) back to the barrel (10) without reducing strength of the safety syringe.

2. Since the wing sections (51) are resilient, the inner needle hub (50) mounted tightly on the spout (11) of the barrel (10) but can be withdrawn into the barrel (10) easily.

3. The current invention is designed on a conventional (non-safety) syringe so machine tools require slight adaptation to allow the safety syringe of the present invention to be produced easily, and with lower precision. Therefore, the manufacture of the safety syringe can be easier and cheaper.

4. The collar (52) of the wing sections (51) can block the inner needle hub (50) being pull into the barrel (10) when the safety syringe draw a injection.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A safety syringe having
a barrel having
   a proximal end;
   a distal end;
   a spout being formed axially on and protruding from the distal end and having an outer diameter;
   an inner diameter; and
   a tapered surface formed on a top of the spout; and
   two finger rests being formed on and protruding oppositely from the proximal end;
a plunger being mounted in the barrel and having
   a distal end; and
   a mounting protrusion being centrally formed axially on the distal end of the plunger and having
     an engaging hole defined in the mounting protrusion and having an inner surface;
     a cross section; and
     an axis;
an outer needle hub being mounted on the spout of the barrel and having
   an inner surface;
   a connecting end;
   a mounting end;
   a hub hole being formed through the connecting end of the outer needle hub; and
   a mounting chamber being formed in the mounting end of the outer needle hub and communicating with the hub hole;
an inner needle hub being mounted in the mounting chamber of the outer needle hub and having
   an outside end;
   an inside end;
   a needle hole defined through the inner needle hub;
   a shoulder formed on and protruding radially from the inner needle hub adjacent to the inside end, larger than and abutting the hub hole of the outer needle hub; and
   at least two wing sections formed on and protruding from the shoulder of the inner needle hub, each wing section being resilient and having
     a collar formed on and protruding at an angle away from the shoulder of the inner needle hub, the collar having an inner slope formed on an end opposite to the shoulder and protruding out from the wing section; and
     an arm formed on, protruding from and with the collar to form a rim there between; and
a needle being hollow and mounted in the needle hole of the inner needle hub; wherein a width of the tapered surface is wider than a width of the inner slope.

2. The safety syringe as claimed in claim 1, wherein the engaging hole has an inner surface and a V-shaped cross section that is parallel with and axially-symmetrical to the axis of the mounting protrusion and the mounting protrusion further has a groove being formed circumferentially around the inner surface of the plunger.

3. The safety syringe as claimed in claim 1, wherein the engaging hole has a distal end, an inner surface and a V-shaped cross section that is inclined to the axis of the engaging hole and the mounting protrusion further has a hook being formed around an end of the mounting protrusion of the plunger.

4. The safety syringe as claimed in claim 2, wherein the inner needle hub is mounted through and extends out of the hub hole of the outer needle hub.

5. The safety syringe as claimed in claim 1, wherein each arm has a tip, and wherein the tips of the arms of the wing sections of the inner needle hub are jointed pivotally.

6. The safety syringe as claimed in claim 2, wherein each arm has a tip, and wherein the tips of the arms of the wing sections of the inner needle hub are jointed pivotally.

7. The safety syringe as claimed in claim 3, wherein each arm has a tip, and wherein the tips of the arms of the wing sections of the inner needle hub are jointed pivotally.

8. The safety syringe as claimed in claim 1, wherein each arm has a tip, and wherein the tips of the arms of the wing sections of the inner needle hub are engaged.

9. The safety syringe as claimed in claim 2, wherein each arm has a tip, and wherein the tips of the arms of the wing sections of the inner needle hub are engaged.

10. The safety syringe as claimed in claim 3, wherein each arm has a tip, and wherein the tips of the arms of the wing sections of the inner needle hub are engaged.

11. The safety syringe as claimed in claim 1, wherein the outer needle hub further has a ring groove being formed in the inner surface of the outer needle hub; and a sealing ring is mounted on the ring groove of the outer needle hub and between the inner needle hub and the outer needle hub.

12. The safety syringe as claimed in claim 2, wherein the outer needle hub further has a ring groove being formed in the inner surface of the outer needle hub; and
   a sealing ring is mounted on the ring groove of the outer needle hub and between the inner needle hub and the outer needle hub.

13. The safety syringe as claimed in claim 1, wherein the safety syringe further has a cover being mounted on the outer needle hub.

14. The safety syringe as claimed in claim 1, wherein the arm of the wing sections is narrower than the collar to form a rim and has an outer surface, wherein the rim has a tapered inner surface defining an inner space.

15. The safety syringe as claimed in claim 1, wherein the arm of the wing sections further has a tip beveled inwards to guide the wing sections into the mounting protrusion of the plunger.

16. The safety syringe as claimed in claim 1, wherein each wing section further has a boss formed on the outer surface of the arm and selectively engaging the groove of the mounting protrusion of the plunger.

17. The safety syringe as claimed in claim 3, wherein the outer needle hub further has a ring groove being formed in the inner surface of the outer needle hub; and a sealing ring is mounted on the ring groove of the outer needle hub and between the inner needle hub and the outer needle hub.

18. The safety syringe as claimed in claim 1, wherein the wing sections are extended in the mounting chamber of the outer needle hub.

* * * * *